United States Patent
Consoli et al.

(10) Patent No.: US 11,534,378 B2
(45) Date of Patent: Dec. 27, 2022

(54) HAIR COLORING COMPOSITIONS

(71) Applicant: BEAUTY & BUSINESS S.p.A., Milan (IT)

(72) Inventors: Antonio Consoli, Urgnano (IT); Katiuscia Grevalcuore, Bergamo (IT); Emanuela Facchetti, Romano di Lombardia (IT)

(73) Assignee: BEAUTY & BUSINESS S.p.A., Milan (IT)

( * ) Notice: Subject to any disclaimer, the term of this patent is extended or adjusted under 35 U.S.C. 154(b) by 241 days.

(21) Appl. No.: 16/787,618

(22) Filed: Feb. 11, 2020

(65) Prior Publication Data

US 2020/0261336 A1     Aug. 20, 2020

Related U.S. Application Data

(60) Provisional application No. 62/807,260, filed on Feb. 19, 2019.

(51) Int. Cl.
*A61Q 5/06*     (2006.01)
*A61K 8/37*     (2006.01)
*A61Q 5/12*     (2006.01)

(52) U.S. Cl.
CPC ............. *A61K 8/375* (2013.01); *A61Q 5/065* (2013.01); *A61Q 5/12* (2013.01); *A61K 2800/432* (2013.01)

(58) Field of Classification Search
None
See application file for complete search history.

(56) References Cited

U.S. PATENT DOCUMENTS

| | | | |
|---|---|---|---|
| 2005/0039269 A1* | 2/2005 | Smith | A61Q 5/10 8/405 |
| 2017/0079901 A1* | 3/2017 | Hippe | A61K 8/84 |
| 2018/0125767 A1* | 5/2018 | Benson | A61Q 5/02 |

* cited by examiner

*Primary Examiner* — Jyothsna A Venkat
(74) *Attorney, Agent, or Firm* — Silvia Salvadori, P.C.; Silvia Salvadori

(57) ABSTRACT

A hair-colouring composition comprising an estolide ester derived from ricinoleic acid and direct dyes.

8 Claims, No Drawings

HAIR COLORING COMPOSITIONS

This non-provisional application claims priority to and the benefit of U.S. Provisional Application No. 62/807,260 filed Feb. 19, 2019, the content of which is incorporated by reference in its entirety.

PRIOR ART

There are two main types of hair-colouring preparation: those that use oxidative dyes and those that use direct dyes.

The technology which uses oxidative dyes is based on the reaction of "primary intermediates" with couplers, both types of molecule being practically colourless. In the presence of air or oxidants such as hydrogen peroxide, primary aromatic amines (primary intermediates) with a hydroxyl or additional amino group, substituted or not substituted, in the para or ortho position, react with resorcinol, m-aminophenol, m-phenylenediamine or 1-naphthol couplers to give various shades of colour. Some years ago, a novel primary intermediate, a substituted 4,5-diaminopyrazole, was introduced onto the market to provide deep red shades with the majority of couplers commonly used. Oxidative dyes preferably function at a basic pH in an interval between 9.5 and 12 in the presence of basic amines, mainly ammonia or alkanolamines, including ethanolamine, but triethanolamine, aminomethyl propanol and aminomethyl propanediol can also be used. With this type of hair-colouring preparation, an oxidation reaction in a basic medium takes place on the hair and near the scalp.

As an alternative to the use of said oxidative dyes, if permanent dyeing with prolonged resistance to washing and high coverage of white hair is not required, but it is desired to change the colour more frequently, hair-colouring preparations containing direct dyes can be used, namely dyes that colour the keratin fibre directly without the aid of a chemical transformation, due to the addition of an oxidising agent. Said dyes are already coloured, and attach to or penetrate the hair due to their affinity with the structure of keratin. The pH required for their use is preferably between 2.5 and 9.5.

Direct dyes can be formulated in the form of solutions, shampoos, gels, creams, conditioners, mousses, and solid anhydrous or water-containing forms.

The hair-colouring process consists of applying the product to the hair and leaving it in contact for a time ranging from 2 to 40 minutes, depending on the desired degree of absorption of the dye by the hair. The longer the contact time with the keratin fibre, the better the absorption will be.

By varying the application times, type of dye, relative concentration and pH, it is possible to obtain products ranging from simple "temporary" dyes which renew and refresh the colour so as to revitalise it or make it brighter and more vibrant, but last for only a few washes, to "semipermanent" dyes which last for up to 10 washes, and can also colour white hair.

In recent years, hair-colouring preparations containing direct dyes have been widely used by the industry as they enable very bright, vivid colours, called "crazy" colours, to be produced, which is very difficult to achieve with the classic oxidation dyeing technique.

Direct dyes are currently in great demand from consumers because they are less aggressive to the skin and hair, as oxidants or strongly basic pHs are not used.

A new market trend is becoming increasingly popular: consumers require a high percentage of naturalness (as defined in ISO 16128-1 of February 2016 and ISO 16128-2 of September 2017) in cosmetic formulas, including those of hair-colouring preparations, as they consider them to be even more gentle to the skin and hair, and to have a lower environmental impact.

However, consumers often do not wish to lose the colouring performance of the conventional product (depth, duration, and colouring white hair) or its cosmetic effect, defined as the set of properties such as moisturisation, easy combing, shine, and a light, silky feel.

For this reason many consumers dislike hair-colouring preparations containing natural dyes (e.g. those based on henna, indigo, turmeric, etc.), because they give a different colour performance. Hair-colouring preparations based on natural dyes require lengthy application times (up to 24 hours). The colour changes with time and washing. After treatment the hair is not very cosmetic, and in particular not well hydrated. Moreover, only a limited number of shades can be obtained with natural dyes.

There is consequently a need to formulate hair-colouring preparations with conventional synthetic direct dyes which offer high performance but are included in compositions based on ingredients of natural origin.

Formulations based on synthetic direct dyes characterised by a fairly high percentage of naturalness already exist on the market, but in order to maintain their good colouring and cosmetic performance they still contain silicones or non-natural conditioning agents in common use such as polyquaternium-7, polyquaternium-22 and polyquaternium-37. Alternatively, formulas with a high percentage of naturalness exist, but are often expensive and offer unsatisfactory cosmetic and colouring performance, especially when white hair is dyed.

For example, IT1425709 describes a cosmetic composition for dyeing keratin fibres comprising at least one direct dye and at least one fatty alcohol derived from esterified *Brassica* L. which produces high absorption of direct dyes by the keratin fibre, thus providing a deep colour, resistant to washing, with a formulation having a high percentage of naturalness.

However, said formulations have a number of drawbacks:

1—fatty alcohols derived from *Brassica* (e.g. brassicyl isoleucinate esylate) only allow formulation in a narrow pH range (3-7, preferably 3.5-5.5), and therefore do not allow the formulation of semipermanent preparations able to colour white hair;

2—fatty alcohols derived from *Brassica* generate formulas with a low level of cosmetic effect on the hair, making the hair heavier (build-up effect), with poor combability and shine;

3—direct dyes formulated with fatty alcohols derived from *Brassica* stain the skin.

The purpose of the present invention is to create a direct dye with a high degree of naturalness, i.e. one containing a high percentage of ingredients with a high natural index as defined in ISO 16128-1 of February 2016 and ISO 16128-2 of September 2017, which allows high absorption of the dyes by keratin fibre (uptake) and good resistance of the colour to washing, without staining the skin or making the hair heavier, but leaving it light, easy to comb and glossy. Said formulation must be versatile in terms of pH, so that hair-colouring preparations can be created in the form of a shampoo, conditioner or semi-permanent dye with a pH up to 9.5, which can also dye white hair.

DETAILED DESCRIPTION OF THE INVENTION

It has surprisingly been found that the problems listed above can be solved by using particular long-chain polyesters, especially those derived from ricinoleic acid, such as ethylhexyl polyricinoleate or lauryl/myristyl polyricinoleate, already known as skin-care emollients and recently introduced onto the hair care market as conditioning agents alternative to silicones and polyquaterniums (WO2016174256).

Surprisingly, the combination of direct dyes and said polyesters derived from ricinoleic acid has proved synergic, promoting the absorption of the direct dye by the keratin fibre and giving a particularly deep colour, resistant to washing, which colours all white hair without staining the skin.

The use of said esters provides moisturisation, easy combing, sheen and lightness to the hair with no need to introduce silicones or non-natural conditioning agents into the formula.

According to a preferred aspect of the invention, the polyester derived from ricinoleic acid consists of lauryl/myristyl polyricinoleate (an ingredient approved by COSMOS on Jan. 1, 2019 under the chemical name of lauryl (poly) ricinoleate).

Lauryl/myristyl polyricinoleate is very cheap, and an amount ranging from 0.5% to 5%, preferably from 0.5% to 1%, by weight of the total weight of the composition is sufficient to give the formula the desired colouring and cosmetic performance.

This enables formulas with a high aqueous content, even containing over 90% water, to be generated.

The formulas are therefore cheap and very natural, with a naturalness range of 96-99.95%.

Said range is calculated by multiplying the natural index of each ingredient (a number from 0 to 1 as specified in ISO 16128-1 of February 2016 and ISO 16128-2 of September 2017) by its percentage weight in the formula, and then totaling all the results obtained.

Lauryl/myristyl polyricinoleate is non-ionic, and therefore allows all types of direct dyes (anionic, cationic and non-ionic) to be formulated, thus offering great versatility in terms of shades.

It also allows a wide range of pH values to be used, ranging from 2.5 to 9.5, thus allowing the creation of hair-colouring preparations in the form of conditioners, shampoos, and even semipermanent dyes, able to colour white hair.

It should be specified that the conditioners according to the invention deposit colour on the hair and refresh/revitalise the natural or cosmetic hair colour. They differ from the colour-care conditioners present on the market, which do not colour the hair but merely protect the cosmetic colour against the fading caused by washing.

The dyes and excipients which can be used in the composition according to the invention are described below, using the chemical name and INCI nomenclature (International Nomenclature of Cosmetic Ingredients, European Community Decision 2006/257/EC, as amended) interchangeably.

The cosmetic composition comprises at least one direct hair dye. The direct dyes can be non-ionic, cationic or anionic.

Examples of direct dyes are Acid green 25, Acid blue 74, Acid blue 3, Acid blue 9, Acid red 18, Acid red 184, Acid red 195, Acid red 27, Acid red 33, Acid red 35, Acid red 51, Acid red 73, Acid red 87, Acid red 92, Acid red 95, Acid violet 43, Acid violet 9, Acid yellow 23, Acid yellow 3, Acid yellow 36, Acid yellow 73, Acid orange 6, Acid orange 7, Acid green 1, Acid green 50, Acid Blue 1, Acid Blue 62, Acid Brown 13, Acid Orange 3, Acid Orange 24, Acid Red 14, Acid Red 35, Acid Red 52, Acid Yellow 1, 2-Amino-6-Chloro-4-Nitrophenol, 4-Amino-2-Nitrodiphenylamine-2'-Carboxylic Acid, 2-Amino-3-Nitrophenol, 2-Amino-4-Nitrophenol, 2-Amino-5-Nitrophenol, 4-Amino-2-Nitrophenol, 4-Amino-3-Nitrophenol, Basic Blue 3, Basic Blue 7, Basic Blue 9, Basic Blue 26, Basic Blue 47, Basic Blue 75, Basic Blue 99, Basic Blue 124, Basic Brown 4, Basic Brown 16, Basic Brown 17, Basic Green 1, Basic Green 4, Basic Orange 1, Basic Orange 2, Basic Orange 31, Basic Red 1, Basic Red 1:1, Basic Red 2, Basic Red 22, Basic Red 46, Basic Red 51, Basic Red 76, Basic Red 118, Basic Violet 1, Basic Violet 2, Basic Violet 3, Basic Violet 4, Basic Violet 10, Basic Violet 11:1, Basic Violet 14, Basic Violet 16, Basic Yellow 28, Basic Yellow 40, Basic Yellow 57, Basic Yellow 87, N,N'-Bis(2-Hydroxyethyl)-2-Nitro-p-Phenylenediamine, 2-Chloro-6-Ethylamino-4-Nitrophenol, 2-Chloro-5-Nitro-N-Hydroxyethyl p-Phenylenediamine, N,N'-Dimethyl-N-Hydroxyethyl-3-Nitro-p-Phenylenediamine, Direct Black 51, Direct Red 23, Direct Red 80, Direct Red 81, Direct Violet 48, Direct Yellow 12, Disperse Black 9, Disperse Blue 1, Disperse Blue 3, Disperse Blue 7, Disperse Blue 377, Disperse Brown 1, Disperse Orange 3, Disperse Red 11, Disperse Red 15, Disperse Red 17, Disperse Violet 1, Disperse Violet 4, Disperse Violet 15, HC Blue No. 2, HC Blue No. 4, HC Blue No. 5, HC Blue No. 6, HC Blue No. 8, HC Blue No. 9, HC Blue No. 10, HC Blue No. 11, HC Blue No. 12, HC Blue No. 13, HC Blue No. 14, HC Blue No. 15, HC Blue No. 16, HC Blue No. 17, HC Blue No. 18, HC Brown No. 1, HC Brown No. 2, HC Green No. 1, HC Orange No. 1, HC Orange No. 2, HC Orange No. 3, HC Orange No. 5, HC Orange No. 6, HC Red No. 1, HC Red No. 3, HC Red No. 7, HC Red No. 8, HC Red No. 9, HC Red No. 10, HC Red No. 11, HC Red No. 13, HC Red No. 14, HC Red No. 15, HC Red No. 17, HC Red No. 18, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, HC Yellow No. 16, HC Yellow No. 17, 2-Hydroxyethylamino-5-Nitroanisole, Hydroxyethyl-2-Nitro-p-Toluidine, 4-Hydroxypropylamino-3-Nitrophenol, 3-Methylamino-4-Nitrophenoxyethanol, 3-Nitro-4-Aminophenoxyethanol, 3-Nitro-p-Cresol, 2-Nitro-5-Glyceryl Methylaniline, 4-Nitroguaiacol, 3-Nitro-p-Hydroxyethylaminophenol, 2-Nitro-N-Hydroxyethyl-p-Anisidine, Nitrophenol, 4-Nitrophenyl Aminoethylurea, 4-Nitro-o-Phenylenediamine, 4-Nitro-m-Phenylenediamine, 4-Nitro-o-Phenylenediamine, 2-Nitro-p-Phenylenediamine, 6-Nitro-2,5-Pyridinediamine, 6-Nitro-o-Toluidine, Pigment Blue 15, Pigment Blue 15:1, Pigment Violet 23, Pigment Yellow 13, Solvent Black 3, Solvent Black 5, Solvent Blue 35, Solvent Yellow 85, Solvent Yellow 172, Tetrabromophenol Blue, Tetrahydro-6-Nitroquinoxaline and Tetrahydropyranyl Resorcinol.

The preferred dyes are Acid blue 9, Acid Red 92, Acid Violet 43, Acid yellow 23, Acid yellow 3, Acid blue 62, Acid red 52, 2-Amino-6-Chloro-4-Nitrophenol: Basic blue 124, Basic orange 31, Basic red 51, Basic violet 2, Basic violet 16, Basic yellow 40, Basic yellow 87, HC blue No. 15, HC blue No. 16, HC red No. 3, HC red No. 10, HC red No. 11, HC yellow No. 2, HC yellow No. 4, 4-Hydroxypropylamino-3-Nitrophenol, 2-Nitro-5-Glyceryl Methylaniline, 3-Nitro-p-Hydroxyethylaminophenol, Tetrabromophenol Blue, Disperse Blue 377, Disperse Violet 1, HC Blue No. 2 and HC blue No 17.

The dyes can be contained in the composition alone or in mixtures, in quantities ranging from about 0.01 to 4.0% by weight of the total weight of the composition.

The composition can also include natural direct dyes, such as those based on lawsone, juglone, alizarine, purpurine, carminic acid, kermesic acid, purpurogallin, protocatechualdehyde, indigo, isatin, curcumin, spinulosine and apigenidine.

The cosmetic composition can also contain one or more natural additives (as defined in ISO 16128-1 of February 2016 and ISO 16128-2 of September 2017), such as solvents, fats, surfactants, thickening agents, triglycerides, alkalinising agents, complexing agents, emulsifiers, emollients, proteins and hydrolysed proteins, amino acids, pigments, polysaccharides (including starches) and oligosaccharides, preservatives and fragrances.

The solvents can be water-soluble organic solvents such as glycols and polyols containing 2 to 6 carbon atoms. The glycols used can be propanediol and butanediol glycols, such as propanediol. Examples of polyols are glycerol, diglycerol, ethylene carbonate and propylene carbonate.

The water-soluble organic solvent can be present in a ready-to-use mixture at the ratio of 10% by weight.

The fats which can be used are of plant origin, the preferred fats being fatty alcohols containing 10 to 30 carbon atoms, such as capric alcohol, lauryl alcohol, myristyl alcohol, cetyl alcohol, stearyl alcohol, behenyl alcohol, oleyl alcohol and brassicyl alcohol.

The fats can be included in the composition in a percentage ranging between 0.1% and 99.95% by weight of the weight of the composition. A high percentage of fats is used in anhydrous formulations.

The surfactants can be cationic, anionic, non-ionic or amphoteric, and can be included in the composition at the ratio of 0.5% to 20.0% of the total weight of the composition.

The non-ionic surfactants which can be used are those containing a lipophilic chain, preferably a C8-C22 straight alkyl or acyl chain, and one or more hydrophilic groups, such as a glucoside or polyglucoside, a glycerol or polyglycerol, or a sorbitan. Examples of non-ionic surfactants which can be used are Coco Glucoside, Decyl Glucoside, Lauryl Glucoside, Capryloyl/Caproyl Methyl Glucamide, Lauroyl/Myristoyl Methyl Glucamide, Lauroyl/Myristoyl Methyl Glucamide and Cocoyl Methyl Glucamide.

Examples of the anionic surfactants which can be used are surfactants characterised by an aliphatic straight chain containing up to 30 carbon atoms, to which a sulphate, sulphonate, phosphate or carboxyl group is bonded. In particular, they can be alkyl sulphates, acyl isethionates, acyl taurates, acyl sarcosinates, sulphosuccinates, alkoylpolypeptides, acyl glutamates, citric and tartaric acid derivatives, carboxylated alkylethers in their alkaline earth metal salt form, magnesium, ammonium or alkanolamines. The composition according to the invention can also contain anionic surfactants in solid state such as dioleyl phosphate and dicetyl phosphate.

Examples of amphoteric surfactants are alkyl betaine, alkylamidopropyl betaine, amphoacetates, amphodiacetates and propionates, preferably cocoamidopropyl betaine (Tego Betain CKD from Evonik) or sodium cocoamphoacetate (DEHYTON MC from BASF).

Examples of cationic surfactants include stearamidopropyl dimethylamine (Chemidex™ S surfactant from Lubrizol) and linoleamidopropyl ethyldimonium ethosulphate (Foamquat CHP). Esterquats such as the following can also be used: Distearoylethyl Hydroxyethylmonium Methosulphate (Dehyquart®F75T from BASF); Dipalmitoylethyl Hydroxyethylmonium Methosulphate (Dehyquart C 4046).

Examples of emulsifiers include cetearyl olivate, sorbitan olivate or a mixture thereof (Olivem 1000 from Hallstar); polyglyceryl-2 stearate, polyglyceryl-2-oleate, glyceryl stearate or mixtures thereof (Polyaquol 2W and Polyaquol OS2); sodium cocoyl alaninate (Eversoft ACS 30S).

The thickening agents can be selected from non-ionic, cationic, anionic or amphoteric agents or mixtures thereof, in amounts ranging from about 0.1% to 10%.

Examples of thickening polymers which can be used are cellulose, carrageenans, alginic acid, alginates, polysaccharides, gum arabic, guar gum, xanthan gum, tara gum and the natural derivatives thereof (as defined in ISO 16128-1 of February 2016 and ISO 16128-2 of September 2017)

The triglycerides which can be used according to the invention are of plant origin and include, for example, almond oil, argan oil, avocado oil, calophyllum oil, castor oil, sesame oil, olive oil, jojoba oil, babassu oil, shea butter, linseed oil and sunflower oil.

The triglycerides are present in quantities ranging from 0.1% to 99.95% by weight of the weight of the composition. High percentages of triglycerides are used for anhydrous formulations.

The composition can contain conditioning agents in addition to lauryl/myristyl polyricinoleate, provided that they are natural as defined in ISO 16128-1 of February 2016 and ISO 16128-2 of September 2017. Some examples are Guar Hydroxypropyltrimonium Chloride; *Trigonella* Foenum-Graecum Hydroxypropyltrimonium Chloride (Fenusoft Q from Vivimed).

The composition can also include proteins or hydrolysed proteins of plant origin, such as soya, almond, pea, potato, linseed, corn and wheat protein or hydrolysed proteins. The hydrolysates can also be derivatised. The hydrolysed proteins or derivatives thereof can preferably be present in the composition in quantities ranging from 0.1 to 10% by weight of the total weight of the composition.

According to a further aspect of the invention, one or more amino acids, preferably arginine, asparagine, glutamine, histidine, lysine, proline and tryptophan, can be added to the composition.

The amino acids can preferably be present in quantities ranging from 0.01 to 10% by weight of the total weight of the composition.

Complexing agents can be included in the composition, provided that they are natural or have a low environmental impact (biodegradable), such as citric acid, potassium citrate, diammonium citrate, phytic acid, sodium gluconate, tetrasodium glutamate diacetate and disodium pyrophosphate.

The quantity of chelating or sequestering agents can range from 0.05% to 5% of the total weight of the composition.

Sunscreens such as titanium dioxide and magnesium oxide can optionally be added to the composition in quantities ranging from 0.01% to 20% of the total weight of the composition.

Preservatives and fragrances can also be added in quantities ranging from 0.01 to 2% of the total weight of the composition.

According to a further aspect of the invention, iron oxides, titanium oxides, zinc oxides, chromium oxides, ultramarines, manganese violet and ferric ferrocyanide can be used as pigments.

The pigments can be added in quantities ranging from 0.01 to 20% of the total weight of the composition. pH correctors such as lactic acid, citric acid, ascorbic acid, sorbic acid and glycolic acid, or alkalinising agents such as arginine, lysine, urea and dimethylglucamine, can also be added.

Other examples of optional ingredients include vitamins, ceramides, plant extracts and essential oils, and antioxidants, provided that they are certified by COSMOS, NATRUE or affiliated organisations.

Said optional ingredients can be present in quantities ranging from about 0.01% to about 5.0% of the total weight of the composition.

The compositions according to the present invention can be formulated as hair-colouring creams, fluid emulsions, gel creams, surfactant-based products, foams (aerosol and non-aerosol) and anhydrous or water-containing solid forms.

The cosmetic composition is a ready-to-use product or mixture designed to be applied to the hair by the following method:
(i) apply the desired quantity to the hair;
(ii) leave to act for a time ranging from 2 to 40 minutes, depending on the desired result;
(iii) optionally use heat sources during step (ii);
(iv) rinse with running water;
(v) optionally blot hair with a towel and dry.

Examples of heat sources which can be used include hairdryers, straighteners, hood dryers or other artificial heat sources.

EXAMPLES

Some examples of compositions according to the invention are set out below.

All the ingredients present in the formulas are selected from those with the highest percentage of naturalness present on the market (as defined in ISO 16128-1 of February 2016 and ISO 16128-2 of September 2017.

The percentage of naturalness of the compositions was calculated as specified in ISO 16128-1 of February 2016 and ISO 16128-2 of September 2017.

Table 1. Example of a composition according to the invention in the form of a colour-depositing conditioner.

TABLE 1

| COLOUR-DEPOSITING CONDITIONER pH 4.5 (COMPOSITION A*) | |
|---|---|
| INGREDIENTS (INCI) | % quantity |
| WATER | Q.s. to 100 |
| CETEARYL ALCOHOL | 4 |
| GLYCERYL STEARATE SE | 2 |
| LAURYL/MYRISTYL POLYRICINOLEATE | 0.5 |
| GLYCERIN | 0.1 |
| POTASSIUM SORBATE | 0.5 |
| COCAMIDOPROPYL BETAINE | 0.1 |
| LACTIC ACID | 0.4 |
| BASIC YELLOW 87 | 0.108 |
| BASIC RED 51 | 0.055 |
| BASIC BLUE 124 | 0.018 |
| CALCULATION OF NATURALNESS | 99.8 |

Table 2. Example of a composition according to the invention in the form of a colour-depositing shampoo.

TABLE 2

| COLOUR-DEPOSITING SHAMPOO pH 6 (COMPOSITION B*) | |
|---|---|
| INGREDIENTS (INCI) | % quantity |
| WATER | Q.s. to 100 |
| SODIUM COCOAMPHOACETATE | 3 |
| COCAMIDOPROPYL BETAINE | 8 |
| LAURYL/MYRISTYL POLYRICINOLEATE | 0.5 |
| GLYCERIN | 0.1 |
| LACTIC ACID | 0.15 |
| FRAGRANCE | 0.5 |
| POTASSIUM SORBATE | 0.5 |
| BASIC YELLOW 87 | 0.108 |
| BASIC RED 51 | 0.058 |
| BASIC BLUE 124 | 0.018 |
| CALCULATION OF NATURALNESS | 99.57 |

TABLE 3

Examples of a composition according to the invention in the form of a semipermanent dye.

| Composition: | C* | D* | E* | F* | G* | H* | I* | L* | M* | N* | O* | P* |
|---|---|---|---|---|---|---|---|---|---|---|---|---|
| INGREDIENTS (INCI) | | | | | | | | | | | | |
| AQUA (WATER) | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 | Q.s. to 100 |
| PROPANEDIOL | 5 | 5 | 5 | 5 | 5 | 5 | 5 | 5 | 5 | 5 | 5 | 5 |
| *CAESALPINIA SPINOSA* GUM | 1.2 | 1.2 | 1.2 | 1.2 | 1.2 | 1.2 | 1.2 | 1.2 | 1.2 | 1.2 | 1.2 | 1.2 |
| LAURYL/MYRISTYL POLYRICINOLEATE | 0.5 | 0.5 | 0.5 | 0.5 | 0.5 | 0.5 | 0.5 | 0.5 | 0.5 | 0.5 | 0.5 | 0.5 |
| GLYCERIN | 0.1 | 0.1 | 0.1 | 0.1 | 0.1 | 0.1 | 0.1 | 0.1 | 0.1 | 0.1 | 0.1 | 0.1 |
| ARGININE | — | — | 0.5 | 0.5 | 0.5 | 0.5 | 0.5 | 0.5 | 0.5 | 0.5 | — | 0.5 |
| LYSINE | — | — | — | — | — | — | — | — | — | — | 1 | 0.5 |
| POTASSIUM HYDROXYDE | 0.5 | 0.5 | 0.2 | 0.2 | 0.2 | 0.2 | 0.2 | 0.2 | 0.2 | 0.2 | 0.2 | 0.1 |
| PHYTIC ACID | 0.1 | — | — | — | — | — | — | — | — | — | — | — |
| UREA | — | 0.1 | — | — | — | — | — | — | — | — | — | — |
| BASIC RED 51 | — | 1 | 0.2 | — | — | 0.1 | — | — | — | — | — | — |
| BASIC YELLOW 87 | 0.108 | — | 0.5 | 0.4 | — | 0.6 | — | — | — | — | — | — |
| BASIC BLUE 124 | 0.018 | — | 0.1 | — | — | 0.5 | — | — | — | — | — | — |
| HC BLUE 16 | — | — | 0.5 | 0.1 | — | — | — | — | — | — | — | — |
| ACID RED 92 | — | 0.2 | — | — | — | — | — | 0.2 | — | — | — | — |
| ACID RED 52 | — | 0.3 | — | — | — | — | — | — | — | — | — | — |
| HC BLUE 2 | — | — | — | — | 1 | — | 1 | — | 1 | — | — | — |
| HC BLUE 15 | — | — | — | — | 0.2 | — | — | — | — | — | — | — |

TABLE 3-continued

Examples of a composition according to the invention in the form of a semipermanent dye.

| Composition: | C* | D* | E* | F* | G* | H* | I* | L* | M* | N* | O* | P* |
|---|---|---|---|---|---|---|---|---|---|---|---|---|
| HC BLUE 17 | — | 0.1 | — | — | — | — | — | — | — | — | — | — |
| HC RED 3 | — | — | — | — | 0.3 | — | — | — | — | — | — | — |
| 3-NITRO-p-HYDROXYETHYLAMINOPHENOL | — | — | — | — | — | 1 | — | — | 0.5 | — | — | — |
| BASIC ORANGE 31 | — | — | — | — | — | — | — | — | — | 0.2 | — | — |
| ACID BLUE 9 | — | — | — | — | — | — | — | 0.1 | — | — | — | — |
| ACID YELLOW 1 | — | — | — | — | — | — | — | 0.15 | — | — | — | — |
| TETRABROMOPHENOL BLUE | — | — | — | — | — | — | — | 0.15 | — | — | — | — |
| HC YELLOW No. 4 | — | — | — | — | — | — | — | — | 0.1 | — | — | — |
| BASIC VIOLET 2 | — | — | — | — | — | — | — | — | — | — | 0.5 | — |
| ACID VIOLET 43 | — | — | — | — | — | — | — | — | — | — | — | 0.5 |
| DISPERSE VIOLET 1 | — | — | — | — | — | — | — | — | — | — | — | 0.1 |
| CALCULATION OF NATURALNESS | | | | | | | | | | | | |

TABLE 4

COMMON COLOR DEPOSITING COMPOSITIONS WITH LOW LEVEL OF NATURALNESS

| Composition: | Q (color-depositing conditioner pH 4.5) | R (semipermanent hair color pH 8.5) |
|---|---|---|
| WATER | Q.s. to 100 | Q.s. to 100 |
| PROPYLENE GLYCOL | 9.1 | 9.1 |
| ETHOXYDIGLYCOL | 5 | 5 |
| CETEARYL ALCOHOL | 4.4 | 4.4 |
| BEHENTRIMONIUM CHLORIDE | 2.4 | 2.4 |
| GLYCERIN | 1.5 | 1.5 |
| GLYCERYL STEARATE | 0.9 | 0.9 |
| CETYL ESTERS | 0.8 | 0.8 |
| ISOPROPYL ALCOHOL | 0.6 | 0.6 |
| CAPRYLYL TRIMETHICONE | 0.5 | 0.5 |
| FRAGRANCE | 0.5 | 0.5 |
| ETHYLHEXYL METHOXYCINNAMATE | 0.3 | 0.3 |
| IMIDAZOLIDINYL UREA | 0.3 | 0.3 |
| AMODIMETHICONE | 0.30 | 0.30 |
| PHENOXYETHANOL | 0.2 | 0.2 |
| BASIC YELLOW 87 | 0.108 | 0.108 |
| BASIC RED 51 | 0.055 | 0.055 |
| ETHYLPARABEN | 0.04 | 0.04 |
| METHYLPARABEN | 0.04 | 0.04 |
| PROPYLPARABEN | 0.02 | 0.02 |
| BASIC BLUE 124 | 0.018 | 0.018 |
| CETRIMONIUM CHLORIDE | 0.01 | 0.01 |
| TRIDECETH-10 | 0.01 | 0.01 |
| LACTIC ACID | 0.01 | — |
| POTASSIUM HYDROXYDE | — | 0.15 |
| CALCULATION OF NATURALNESS | 80.5 | 80.5 |

TABLE 5

COLOR-DEPOSITING CONDITIONER WITH BRASSICA DERIVED FATTY ALCHOL

| Composition: | S (pH 4.5) |
|---|---|
| WATER | Q.s. to 100 |
| *BRASSICA* ALCOHOL | 8.0 |
| BRASSICYL ISOLEUCINATE ESYLATE | 3.0 |
| CAPRYLYL GLYCOL | 1.0 |
| GLYCERIN | 0.65 |
| GLYCERYL CAPRYLATE | 0.15 |
| PHENYLPROPANOL | 0.1 |
| ARGININE | 0.05 |
| BASIC YELLOW 87 | 0.108 |
| BASIC RED 51 | 0.055 |
| BASIC BLUE 124 | 0.018 |
| CALCULATION OF NATURALNESS | 99.8 |

NOTE:
it is not possible to formulate a semipermanent hair color at basic pH with *brassica* derived fatty alchol Shine Test To perform this test IHIP swatches level 6 (natural dark blonde hair) were used.

The swatches were coloured with the different compositions

After 20 minutes of application time the swatches were washed with tap water at about 37° C. until the water run clear. The swatches were combed and dryed for 30 minutes at 60° C.

To evaluate the shine the SAMBA Hair System tool from Bossanova Technologies was used.

A specific algorithm called Bossa Nova Technologies (BNT) produced the shine values reported in table 6. The higher the value, the greater the shine

TABLE 6

SHINE PERFORMANCE

| COMPOSITION | BNT |
|---|---|
| A* | 31.10 |
| Q | 29.23 |
| S | 15.52 |
| C* | 36.71 |
| R | 27.94 |

Among the colour-depositing conditioners the Composition A* (according to the invention) demonstrates a better shine while the composition S is the worst. Regarding the semipermanent dyes, composition C* (according to the invention) has a better shine than composition R.

Combing Test

To perform this test IHIP swatches level 6 (natural dark blonde hair) were used.

The swatches were coloured with the different compositions

After 20 minutes of application time the swatches were washed with tap water at about 37° C. until the water run clear. The swatches were combed and dried for 30 minutes at 60° C.

To evaluate the combing we used a instrument called DIA-STRON MTT175.

The instrument gives data about the work to make a combing on swatches.

The value is shown in Joule. The smaller the value, the less work is needed to comb the swatch so the better is the combability

TABLE 7

| COMBABILITY PERFORMANCE | |
| --- | --- |
| COMPOSITION | JOULE (E-03) |
| A* | 3.36 |
| Q | 5.22 |
| S | 42.1 |

Composition A* has the best combability compared with composition Q and S. In particular the composition S (with *brassica* derived fatty alcohol) has a very bad profile.

Vibrancy Test

To perform this test IHIP swatches level 6 (natural dark blonde hair) were used.

The swatches were bleached using bleaching powder Alfaparf Equipment Supermeches 9 levels and Alfaparf Oxid'o 30 vol (mixing ratio 1:2)

After 35 minutes of developing time in a climatic chamber at 30° C. the swatches were carefully rinsed with running tap water and dried for 30 minutes at 60° C.

The swatches were then coloured with the different compositions.

After 20 minutes of application time the swatches were washed with tap water at about 37° C. until the water run clear. The swatches were combed and dried for 30 minutes at 60° C.

The vibrancy of colour was evaluated using a Spectrophotometer Konica Minolta CM-2500d.

In the CIELAB color space, L* indicates lightness while a and b are the chromaticity coordinates. a* and b* indicate the directions of the color, +a* is the direction of red, −a* is the direction of green, +b* is the direction of yellow and −b* is the direction of blue.

To evaluate the vibrancy we considered the parameter a (direction of red), the higher the value, the greater the vibrancy, which is the brilliance of the colour (the opposite of opaque)

TABLE 8

| VIBRANCY PERFORMANCE | |
| --- | --- |
| COMPOSITION | VIBRANCY (a value) |
| A* | 12.2 |
| Q | 6.53 |
| S | 12.18 |

The Composition A* has a greater vibrancy than composition Q that is a common technology with low level of naturalness. The Composition S and A* have a similar vibrancy.

The invention claimed is:

1. A hair-colouring composition comprising an estolide ester derived from ricinoleic acid and direct dyes, said hair-colouring composition having a naturalness range of 96-99.95%.

2. The hair-colouring composition as claimed in claim 1, wherein the estolide ester derived from ricinoleic acid is lauryl/myristyl polyricinoleate.

3. The hair-colouring composition as claimed in claim 2, wherein lauryl/myristyl polyricinoleate is in an amount from 0.5% to 5%, by weight of the total weight of the composition.

4. The hair-colouring composition as claimed in claim 2, wherein lauryl/myristyl polyricinoleate is in an amount from 0.5% to 1% by weight of the total weight of the composition.

5. The hair-colouring composition as claimed in claim 1 having a pH ranging from 2.5 to 9.5.

6. The hair-colouring composition as claimed I claim 1 in form of conditioners, shampoos or semipermanent dyes.

7. The hair-colouring composition as claimed in claim 1, wherein the direct dyes are non-ionic, cationic or anionic.

8. A method of coloring hair comprising application of a hair-coloring composition as claimed in claim 1 to hair for a time ranging from 2 to 40 minutes and optional application of heat, followed by washing said hair with water.

* * * * *